US011154199B2

(12) United States Patent
Hendriks et al.

(10) Patent No.: US 11,154,199 B2
(45) Date of Patent: Oct. 26, 2021

(54) IMAGING SYSTEM WITH HYPERSPECTRAL CAMERA GUIDED PROBE

(71) Applicant: KONINKLIJKE PHILIPS N.V., Eindhoven (NL)

(72) Inventors: Bernardus Hendrikus Wilhelmus Hendriks, Eindhoven (NL); Johannes Joseph Hubertina Barbara Schleipen, Eindhoven (NL); Christian Reich, Eindhoven (NL); Gerhardus Eilhelmus Lucassen, Eindhoven (NL); Manfred Mueller, Eindhoven (NL); Vishnu Vardhan Pully, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 809 days.

(21) Appl. No.: 14/653,554

(22) PCT Filed: Jan. 22, 2014

(86) PCT No.: PCT/IB2014/058455
§ 371 (c)(1),
(2) Date: Jun. 18, 2015

(87) PCT Pub. No.: WO2014/118674
PCT Pub. Date: Aug. 7, 2014

(65) Prior Publication Data
US 2016/0007858 A1 Jan. 14, 2016

Related U.S. Application Data

(60) Provisional application No. 61/758,312, filed on Jan. 30, 2013.

(51) Int. Cl.
*A61B 5/00* (2006.01)
*G06T 7/70* (2017.01)
(Continued)

(52) U.S. Cl.
CPC .......... *A61B 5/0077* (2013.01); *A61B 5/0035* (2013.01); *A61B 5/0059* (2013.01);
(Continued)

(58) Field of Classification Search
CPC combination set(s) only.
See application file for complete search history.

(56) References Cited

U.S. PATENT DOCUMENTS

| 7,013,172 B2 | 3/2006 | Mansfield et al. |
| 8,320,996 B2 | 11/2012 | Panasyuk et al. |

(Continued)

FOREIGN PATENT DOCUMENTS

| CN | 101455559 A | 6/2009 |
| CN | 101617935 A | 1/2010 |
| CN | 101785663 A | 7/2010 |

OTHER PUBLICATIONS

Yuen, P.W.T. et al, "An introduction to hyperspectral imaging and its application for security, surveillance and target acquisition", The Imaging Science Journal, vol. 58, 2010, p. 241-253.
(Continued)

Primary Examiner — Amelie R Davis
Assistant Examiner — Marjan Saboktakin (57) ABSTRACT

A medical imaging system for identifying a target structure (TS), e.g. a tumor, in a biological tissue. A hyperspectral camera system is used for imaging a surface area (A1) of the tissue (BT), e.g. with a limited spectral resolution, but enough to allow identification of suspicious areas where the target structure (TS) may be, e.g. such areas can be visually indicated on a display to the operator. A probe (PR), e.g. an optical surface probe, is used to provide probe measurement of a smaller surface area (A2) of the tissue, but with more information indicative of the target structure. The probe is selected to provide a higher specificity with respect to
(Continued)

identification of the target structure than the hyperspectral camera (HSC). The hyperspectral processing algorithm (PP) is then calibrated based on probe measurement data performed within the suspicious areas, thus providing a calibrated hyperspectral processing algorithm resulting in images with an enhanced sensitivity to identify the target structure. Only few probe measurements are required to significantly improve the resulting image, thereby providing a reliable and fast target structure (TS) identification.

20 Claims, 5 Drawing Sheets (51) Int. Cl.
*A61B 8/12* (2006.01)
*A61B 5/1455* (2006.01)
*G01J 3/02* (2006.01)
*G01J 3/28* (2006.01)

(52) U.S. Cl.
CPC .......... *A61B 5/0066* (2013.01); *A61B 5/0068* (2013.01); *A61B 5/0071* (2013.01); *A61B 5/0075* (2013.01); *A61B 5/0084* (2013.01); *A61B 5/742* (2013.01); *A61B 8/12* (2013.01); *G01J 3/0218* (2013.01); *G06T 7/70* (2017.01); *A61B 5/1455* (2013.01); *A61B 2560/0223* (2013.01); *A61B 2576/00* (2013.01); *G01J 3/2823* (2013.01); *G06T 2207/10064* (2013.01); *G06T 2207/30096* (2013.01)

(56) References Cited

U.S. PATENT DOCUMENTS

| 2007/0024946 | A1* | 2/2007 | Panasyuk | A61B 5/0059 359/253 |
| 2009/0326383 | A1* | 12/2009 | Barnes | A61B 5/0059 600/476 |
| 2012/0050321 | A1 | 3/2012 | Arieli et al. | |
| 2013/0003064 | A1* | 1/2013 | Allen | G01J 3/28 356/402 |

OTHER PUBLICATIONS

Nachabe, R. et al., "Estimation of biological chromophores using diffuse optical spectroscopy: benefit of extending the UV-VIS wavelength range to include 1000 to 1600 nm," Optics Express, vol. 18, 2010, pp. 879-888.

Nachabe, R. et al., "Estimation of lipid and water concentrations in scattering media with diffuse optical spectroscopy from 900 to 1600 nm," Journal of Biomedical Optics, vol. 15, May 2010, pp. 037015-10.

Shaw, G.A. et al., "Spectral imaging for remote sensing", Lincoln Laboratory Journal 14 (1), 2003, pp. 3-28.

"Osy Vu Hyperspectral Imaging Technology". www.hypermed-inc.com.

Panasyuk, S.V. et al., "Medical hyperspectral imaging to facilitate residual tumor identification during surgery.", 2007, Cancer Biology & Therapy 6(3): 439-446.

Akbari, H. et al., "Cancer detection using infrared hyperspectral imaging", 2011, Cancer Science 102(4) 852-857.

Lue, N. et al. "Portable optical fiber probe-based spectroscopic scanner for rapid cancer diagnosis: A new tool for intraoperative margin assessment", PLos ONE 7(1): e30887.

Hamada, K. et al. "Raman microscopy for dynamic molecular imaging", J. Biomed Optics. 13(4), 044027 (104) (2008).

Nachabe, R. et al. "Diagnosis of breast cancer using optical spectroscopy from 500 to 1600 nm: a comparison of classification methods", J. Biomed. Opt. 16(2011) p. 087010.

Hendriks, B.H.W. et al., "High resolution resonant and non resonant fiber-scanning confocal microscopy", J. Biomed. Opt. 16(2011) p. 026007.

Carlson, K. et al., "In vivo fiber-optic confocal reflectance microscope with an injection-molded plastic miniature objective lens," Appl. Opt. 44(10), 1792-1797 (2005).

Jung, J.C. et al. , "In vivo mammalian brain imaging using one-and twoo-phton fluorescence microendoscopy," J. Neurophysiol. 92(5), 3121-3133 (2004).

Jung, J. C. et al., "Multiphoton endoscopy," Opt. Lett. 28(11), 902-904(2003).

Myaing, M.T. et al., "Fiber-optic scanning two-photon fluorescence endoscope," Opt. Lett. 31(8), 1076-1078 (2006).

Tearney, G.J. et al., "In vivo endoscopic optical biopsy with optical coherence tomography," Science 276(5321), 2037-2039 (1997).

Farrell, T. J. et al., "A diffusion theory model of spatially resolved, steady-state diffuse reflectance for the non-invasive determination of tissue optical properties," Med. Phys. 19(1992) p. 879-888.

Mueller, M. et al., "Modeling electrophoretic paper like displays", Proc. IDW 1-3, 1287-1290 (2007).

Zhang, Q. et al., "Turbidity free fluorescence spectroscopy of biological tissue", Opt. Lett. 25 (2000) p. 145.

Hohmann, M. et al. "Preliminary results for hyperspectral videoendoscopy diagnostics on the phantoms of normal and abnormal tissues: towards gastrointestinal diagnostics", Clinical and Biomedical Spectroscopy and Imaging II, proceedings of the SPIE, vol. 8087, pp. 80872N-80872N-6 (2011).

* cited by examiner

IMAGING SYSTEM WITH HYPERSPECTRAL CAMERA GUIDED PROBE

CROSS-REFERENCE TO PRIOR APPLICATIONS

This application is the U.S. National Phase application under 35 U.S.C. § 371 of International Application Serial No, PCT/IB2014/058455, filed on Jan. 22, 2014, which claims the benefit of U.S. Application Ser. No. 61/758,312, filed on Jan. 30, 2013. These applications are hereby incorporated by reference herein.

FIELD OF THE INVENTION

The present invention relates to the field of medical devices or equipment. More specifically, the invention relates to a medical imaging system and a method for identifying a target structure in biological tissue, such as for effective tumor margin assessment.

BACKGROUND OF THE INVENTION

During tumor resection surgery the evaluations of the boundaries of the resected tissue whether they are tumor free is of vital importance. When the tumor is not complete resected the treatment will not be curative with all devastating consequences for the patients. Although histopathology is the gold standard for evaluating whether the resection was complete, this can only be done after the surgery has been completed because of the time required for the evaluation of the resected specimen. Although surface probes are under development that can investigate the outer layer of the resected tissue to a certain depth for positive margins, these methods are still rather time consuming because the exterior surface has to be investigated with sufficient accuracy and with sufficient resolution. Furthermore, since these measurements are point like (or small area measurements) they are prone to fluctuations because of heterogeneous tissue structure that may render these measurements less stable.

The problem is thus how to inspect the surface of a resected tumor tissue for positive margins in a time efficient and a robust way.

SUMMARY OF THE INVENTION

It would be advantageous to provide a system and method allowing a stable and at the same time efficient identification of a target structure, e.g. tumor tissue, within a biological tissue.

In a first aspect, the invention provides a medical imaging system arranged to identify a target structure in an associated biological tissue, the system comprising
 a hyperspectral camera system arranged to provide a hyperspectral image covering a first surface area of the biological tissue, wherein pixels of the hyperspectral image contains information at different light wavelength bands,
 a probe arranged to provide a probe measurement of a second surface area of the biological tissue with information indicative of the target structure, and to generate probe measurement data accordingly, wherein the second surface area is smaller than the first surface area, and wherein the probe is selected to provide a higher specificity with respect to identification of the target structure than the hyperspectral camera system, and
 a processor functionally connected to receive the hyperspectral image and the probe measurement data, wherein the processor is arranged to analyze the hyperspectral image according to a hyperspectral processing algorithm in order to identify a part of the hyperspectral image which possibly contains the target structure, wherein the processor is further arranged to analyze the probe measurement data and to calibrate the hyperspectral processing algorithm in response thereto, so as to provide a calibrated hyperspectral processing algorithm with an enhanced sensitivity to identify the target structure in the hyperspectral image.

The invention solves the mentioned problem in that the hyperspectral image can be used to provide an image of a sufficiently large area very quickly, but with a rather limited spectral resolution, and thus a rather low specificity regarding identification of the target structure within the biological tissue. However, still the hyperspectral image can be used to identify suspicious areas, i.e. areas where it can be expected that there is a certain possibility that the target structure is present. The hyperspectral image can then be used by the operator, e.g. by means of a visual indication on a display, as a guide towards selecting which location(s) within the first surface area covered by the hyperspectral image to be measured by a probe selected such that it provides a higher specificity with respect to identification of the target structure. Thus, the probe provides better data for identifying the target structure, e.g. by providing a higher spectral resolution than the hyperspectral image, but at the price of a limited measurement area, e.g. in the form of point or point-like measurements. Using the probe measurement data to modify or calibrate the hyperspectral image processing algorithm, an improved image with enhanced contrast and/or sensitivity with respect to identify the target structure, e.g. tumor tissue, can be obtained. After one or a limited number of probe measurements have been performed, and the hyperspectral image processing algorithm has been calibrated accordingly, the real-time hyperspectral images processed with the calibrated algorithm can be used to provide very quick inspection of further target structures.

Thus, the high speed of the hyperspectral camera is used to point out suspicious area to be examined with the more time consuming probe. However, it turns out that even one single point-like probe measurement can be used to significantly improve the hyperspectral image towards increasing sensitivity to identify the target structure. In this way, the medical imaging system according to the invention can provide a robust and time efficient identification of positive margins after resection. This allows the system to be used during surgery and thus increases the chance of removing all tumor tissue during oncological surgery without the need to redo the surgery, if it turns out at a later examination that not all tumor tissue had been successfully removed. It is to be understood, that the type of probe and subsequent processing of the probe measurement data should preferably be selected towards providing a high sensitivity towards identifying the specific target structure in question.

In the case of identifying a tumor, the hyperspectral camera system can be used to make visible images and hyperspectral images of the surface of the tissue specimen, a contact probe or surface probe capable of measuring locally inside the tissue near the surface of the specimen. The hyperspectral images are analyzed for suspicious areas based on look-up-table data and capable of analyzing the probe for suspicious signatures. The probe is capable of producing a signal indicative whether the probed surface contains a positive margin, and the area to be inspected with the surface probe is indicated in the visible image based on the hyperspectral image analysis. E.g. signals from the surface probe, taken at a few locations, are used to calibrate the 2D-image processing algorithms used for analyzing the hyperspectral images. The probe data may especially be acquired with a larger spectral range, with higher spectral resolution, and may also cover part of the tissue below the surface, hence allowing an accurate assessment of these tissue points. The idea is that these surface probe measurements needs to be done only a few times during an intervention (e.g. when the 2D-spectral image processing indicates a large reconstruction uncertainty), and that once this calibration with the surface probe data has been performed and the system is re-calibrated, the operator can use the real-time 2D results obtained from the hyperspectral images according to the invention. Especially, the signals of the surface probe measurements are annotated in the visible image and or hyperspectral image based on image analysis of the visible image to register the probe tip location with the specimen at the time of measurement.

Apart from identifying tumor tissue, the imaging system can also be used to identify other target structure, e.g. the presence of blood vessels, nerve bundles and the like below the surface of biological tissue, e.g. during surgery. Hereby it is possible to avoid an accidental section of such blood vessels and nerve bundles within the need for a time consuming and/or interventional probes.

In a preferred embodiment, the probe measurement is acquired with a higher spectral resolution than the hyperspectral image. Especially, the hyperspectral image may be acquired with overlapping spectral bands of a rather low spectral resolution, or the spectral bands can be non-overlapping and thus have spectral bands without any information. Thus, in both cases, the probe may provide measurement data with a higher spectral resolution which thus allows a higher specificity with respect to identify the target structure within the biological tissue.

It is preferred that the second surface area is selected to be located within the first surface area, and thus that the probe measurement is performed within the area covered by the hyperspectral image. In case the probe is an interventional device, it is to be understood that by "within the first surface area" is understood that the probe measurement is performed in a point or small area in the biological tissue below the surface of the first surface area.

The system may be arranged to visually display the hyperspectral image after being processed with the hyperspectral processing algorithm together with a visual indication of the part which is. E.g. special shading, coloring, highlighting, or encircling can be used to graphically indicate the part or parts which are identified as possibly containing the target structure.

The system is preferably arranged to visually display the hyperspectral image after being processed with the calibrated hyperspectral processing algorithm. Hereby, the operator, e.g. a physician, can inspect the resulting hyperspectral image, which after processing by the calibrated algorithm is now enhanced with respect to better visualize the target structure.

The processor may be arranged to analyze the probe measurement data according to a probe processing algorithm comprising comparing the probe measurement data with a look-up-table. Alternatively or additionally, the processor may be arranged to analyze the probe measurement data according to a probe processing algorithm comprising calculating a plurality of measurement parameters and translating the plurality of measurement parameters into physiological parameters indicative of the target structure.

The processor may be arranged to calibrate the hyperspectral processing algorithm by refining a grouping of pixels in the hyperspectral image which are identified in the probe measurement data as belonging to the target structure. Such improved grouping of pixels in the hyperspectral image will provide an enhanced visualization of the target structure. E.g. the grouping of pixels assigned with the same color or brightness may be changed or tuned based on parameters extracted from the probe measurement data.

The probe may comprise a surface probe, and/or an interventional device. The probe may comprise an optical probe, and/or an ultrasound probe. The selection of which probe to use depends on the type of biological tissue and the target structure to be identified therein. Especially the optical probe may comprise one of: a diffuse reflectance spectroscopy probe, a diffuse optical tomography probe, a differential path length spectroscopy, a fluorescence probe, a Raman spectroscopy probe, a confocal reflectance probe, a confocal fluorescence probe, a two-photon fluorescence probe, an optical coherence tomography probe, and a scanning fiber microscope arranged to perform confocal imaging.

Preferably, the hyperspectral camera system is arranged to provide two-dimensional real-time images, thus allowing real-time navigation of the probe tip if the hyperspectral images are display on a monitor to the probe operator. The hyperspectral camera system may in general be based on one of: (1) a dedicated hyperspectral camera which, based on light from a broadband light source, has wavelength separation inside the camera, (2) a light source with tunable wavelength or tunable filter set and a normal camera, and (3) a broadband light source and a tunable filter in front of normal camera.

The hyperspectral cameras, i.e. type (1), are typically expensive, while type (2) and (3) are based on a normal camera. However, they suffer from other advantages. E.g. the solution with illumination with different wavelength lights which requires the environments to be dark to produce high quality images. See "An introduction to hyperspectral imaging and its application for security, surveillance and target acquisition", P. W. T. Yuen, M. Richardson, The Imaging Science Journal, Vol. 58, 2010, p. 241-253 regarding hyperspectral camera systems. Thus, in one embodiment, the hyperspectral camera system comprises one of:
  a hyperspectral camera arranged to provide the hyperspectral image,
  a normal camera and a plurality of light sources with different narrow band wavelengths and a controller arranged to provide images with the biological tissue sequentially illuminated by the plurality of light sources, and
  a normal camera and a tunable optical filter arranged between the normal camera and the biological tissue, so as to provide sequential images with different settings of the tunable optical filter.

The processor may be arranged to process the hyperspectral image according to an image processing algorithm in order to identify a tip of the probe in the hyperspectral image, so as to identify to which part of the hyperspectral image the probe measurement data corresponds. In this embodiment, it is possible to automatically identify to which part of the hyperspectral image a given probe measurement applies, which is preferred in order to perform the calibration of the hyperspectral processing algorithm in a fast and reliable manner compared to other types of location means for determining the location of the probe during measurement.

As already mentioned, the imaging system can be used for identification of different target structures, such as: tumor tissue, a nerve bundle, a blood vessel (artery or vein), lymph nodes, and oxygenation level of tissue.

It is to be understood that the processor is preferably controlled by a control algorithm which can be implemented as a software program arranged for execution on a suitable processor system or computer. The processor of the system may be implemented in a dedicated device, e.g. including a display to display the hyperspectral images, or the processor of the system may be implemented as a software program arranged to execution on a server or a general purpose computer.

The size and shape of the interventional device and/or surface probe, such as thickness and number of the optical fibers in case of an optical probe, is understood to be selected for a given application.

In a second aspect, the invention provides a method for detecting a target structure in an associated biological tissue, the method comprising providing a hyperspectral image covering a first surface area of the associated biological tissue, wherein pixels of the hyperspectral image contains information regarding different light wavelength bands, providing probe measurement data in accordance with a probe measurement of a second surface area of the biological tissue with information indicative of the target structure, wherein the second surface area is smaller than the first surface area and located within the first surface area, and wherein the probe measurement is selected to provide a higher specificity with respect to identification of the target structure than the hyperspectral camera system, analyzing the hyperspectral image according to a hyperspectral processing algorithm in order to identify a part of the hyperspectral image which may contain the target structure, analyzing the probe measurement data, and calibrating the hyperspectral processing algorithm in response to a result of the probe measurement data analysis, so as to provide a calibrated hyperspectral processing algorithm with an enhanced sensitivity to identify the target tissue structure in the hyperspectral image.

It is understood that "providing" hyperspectral image and "providing" probe measurement data covers a version of the method where "providing" means merely receiving data, e.g. in digital format, e.g. stored or transmitted data. However, in another version of the method, "providing" covers actually taking the hyperspectral image of the biological tissue, and also performing the probe measurement on the biological tissue.

It is appreciated that the same advantages and embodiments of the first aspect apply as well for the second aspect. In general the first and second aspects may be combined and coupled in any way possible within the scope of the invention. These and other aspects, features and/or advantages of the invention will be apparent from and elucidated with reference to the embodiments described hereinafter.

It is to be understood that the system according to the first aspect and the method according to the second aspect can be used in a number of applications, such as: identification of a positive margin after oncological surgery, identification of blood vessels (artery or vein) below a tissue surface, identification of a nerve bundle below a tissue surface, lymph nodes, and oxygenation level of tissue.

BRIEF DESCRIPTION OF THE DRAWINGS

Embodiments of the invention will be described, by way of example only, with reference to the drawings, in which.

DESCRIPTION OF EMBODIMENTS

Figure 1:
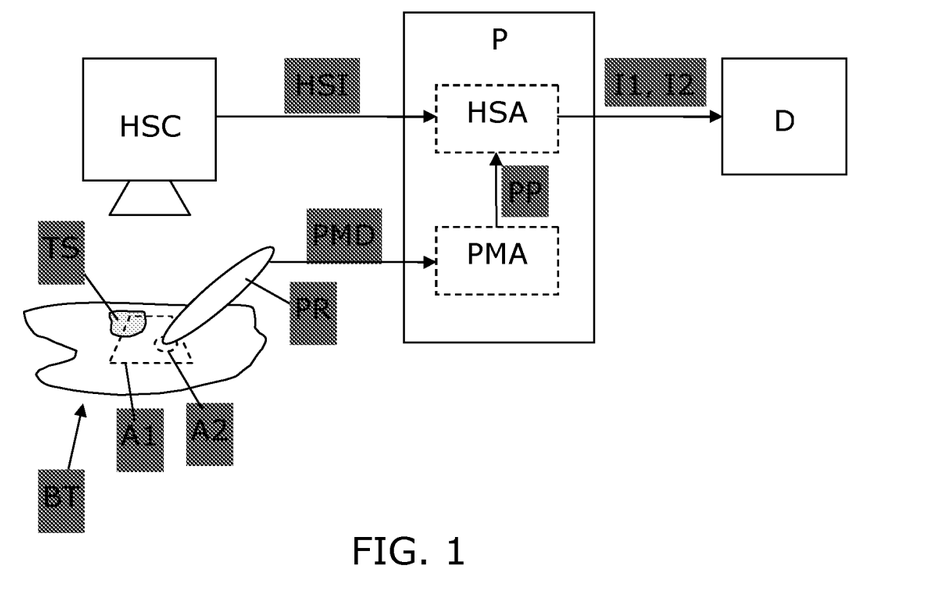
FIG. 1 illustrates a simple block diagram of an imaging system embodiment.

FIG. 1 illustrates basic parts of a system embodiment with a hyperspectral camera HSC real-time 2D hyperspectral images HSI which are applied to a processor P and processed in a hyperspectral processing algorithm HSA. The hyperspectral camera HSC provides a hyperspectral image of a first area A1 of a biological tissue BT to be tested, e.g. a part of a human body to be tested with respect to the presence of a target structure in the form or tumor tissue TS. The hyperspectral image after processing I1 is then displayed in color or grey shadings on a display D, e.g. with a visual indicators graphically highlighting suspicious parts of the image which are identified as possible for containing tumor tissue TS.

An optical surface probe PR provides probe measurement data PMD of a single measurement covering a second area A2 located within the first area A1 covered by the camera HSC. The probe measurement data PMD are applied to the processor and processed by a probe measurement algorithm PMA. This algorithm PMA may include extracting one or more physiological parameters PP based on the probe measurement data PMD. The probe is selected such that it provides measurement data PMD with a higher specificity with respect to identifying the tumor tissue TS, e.g. by providing a higher spectral resolution than the hyperspectral camera HSC. Thus, even though the probe PR covers a limited area A2, e.g. a single point, it provides probe measurement data PMD including information that allows identification of the tumor tissue TS with a higher certainty than possible based on the hyperspectral image, e.g. due to a measurement technique allowing information further below the tissue surface than it is possible with a hyperspectral image.

The physiological parameters PP extracted from the probe measurement data PMD are used to calibrate the hyperspectral processing algorithm HSA, e.g. by refining the grouping of image pixels in the hyperspectral image in order to better visually enhance physiological structures of the tumor tissue in the hyperspectral image. This results in a calibrated hyperspectral processing algorithm HSA, and the subsequently processed hyperspectral images 12 are then displayed on the display D, thus resulting in an image where tumor tissue TS relevant structure are visually enhanced, thus allowing the operator to more clearly identify tumor tissue TS. However, the hyperspectral image allows identification of parts of the area A1 covered where there is a possibility that tumor tissue is present, and this can be used as a guide for an operator towards selecting the point or area A2 to perform probe measurements, thus saving time consuming probe measurements covering the whole area A1. Especially, probes PR providing point measurements can be used which allow a very high specificity with respect to identification of tumor tissue TS, thus providing a highly reliable identification of tumor tissue TS within the first area A1 at a high speed.

The probe can be a surface probe or an interventional device. In case the probe is an optical probe, optical fibers of the probe are preferably connected to an optical console. In a specific embodiment, the optical detector can resolve light with a wavelength substantially in the visible and infrared regions of the wavelength spectrum, such as from 400 nm to 1700 nm and it may allow for diffuse reflectance measurements in both the visible and the near infrared wavelength range. For a detailed discussion on diffuse reflectance spectrum (DRS) measurements see R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm," Optics Express, vol. 18, 2010, pp. 879-888, and R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm," Journal of Biomedical Optics, vol. 15, May. 2010, pp. 037015-10.

The information regarding the progress and whether the area under A1 under test contains tumor tissue can be provided in several ways by the processor P to the operator, e.g. a physician. For instance a light indicator or an indication on the display D can be used that when showing a red light still tumor tissue is detected and with green light no tumor and/or optionally with yellow light suspects tumor. Another way is using an audible sound signal. Yet another way of informing the operator of the result is to calculate a probability of tumor detection by means of a graphical indication on the display D, such as a bar and/or with numbers and/or colors.

Since the hyperspectral camera HSC provides real-time images, it is possible to visually indicate the presence of the probe in the displayed image, thus allowing the operator to place the probe in the suspicious area and perform the probe measurements therein. The processor may then include an image processing algorithm allowing a detection of the probe tip, so as to automatically assign the probe measurement data PMD to the correct location within the hyperspectral image.

In hyperspectral imaging a 2D-image of a distant object is taken, whereby for each pixel of the 2D-image the spectral content of the registered photons is being analyzed. This effectively results in a 3D-data set where the image intensity is stored as function of (X,Y)-coordinate and wavelength. Although originally developed for space borne and airborne applications (mineralogy, agriculture) requiring highly sensitive and expensive imaging systems, hyperspectral imaging cameras are now commercially available for the professional and consumer market, and are also being applied in e.g. healthcare and surveillance. Depending on the required field-of-view, frame-rate and the number and width of the spectral windows, different technologies are being used based on point-scanning or line-scanning devices and diffractive, refractive or interferometric spectral filtering. A typical example of a hyperspectral imaging camera is shown in FIG. 1 illustrating two hyperspectral cameras from manufacturers Headwall and Horiba. A more detailed overview of hyperspectral imaging can be found in Shaw G. A.; Burke H. K., "Spectral Imaging for Remote Sensing", Lincoln Laboratory Journal 14 (1), 2003, pp. 3-28.

For healthcare applications, Medical Hyperspectral Imaging (MHSI) is typically used to provide two-dimensional tissue oxygenation maps. During imaging, reflected light can be collected at multiple wavelengths and processed to separate the oxy- and deoxyhemoglobin signals, and dedicated algorithms can be used to display data in an oxygenation map of tissue viability HyperMed Inc. "OxyVu Hyperspectral Imaging Technology." from www.hypermed-inc.com. Recently, hyperspectral imaging systems with dedicated algorithms for identifying areas with indications for the presence of tumor tissue have been introduced [Panasyuk, S. V., S. Yang, et al. (2007). "Medical hyperspectral imaging to facilitate residual tumor identification during surgery." Cancer Biology & Therapy 6(3): 439-446], and [Hamed Akbari, Kuniaki Uto, Yukio Kosugi, Kazuyuki Kojima and Naofumi Tanaka (2011), Cancer detection using infrared hyperspectral imaging, Cancer Science 102 (4) 852-857]. These systems image surface areas either in the visible wavelength range from 400 nm up to 800 nm [Panasyuk, S. V., S. Yang, et al. (2007). "Medical hyperspectral imaging to facilitate residual tumor identification during surgery." Cancer Biology & Therapy 6(3): 439-446] or in the near-infrared range (1000-2500 nm) [Hamed Akbari, Kuniaki Uto, Yukio Kosugi, Kazuyuki Kojima and Naofumi Tanaka (2011), Cancer detection using infrared hyperspectral imaging, Cancer Science 102 (4) 852-857] and color the image according to a look-up table to identify suspicious spots.

However, the sensitivity is often hampered by the presence of extravagating blood on the tissue surface, which commonly occurs in open surgery. The limited wavelength range and spectral resolution also limit the specificity, since the major distinguishing parameters are blood content and blood oxygenation, and tumor discriminators which are less prominent in the visible wavelength range (such as tissue scattering and absorption by bile, water, fat, and others) may not be properly considered.

In some embodiments, the hyperspectral camera system can be arranged to obtain high spectral images using line scanning images, see e.g. [K. Hamada, K. Fujita, N. I. Smith, M. Kobayashi, and S. Kawata, "Raman microscopy for dynamic molecular imaging", J Biomed Optics. 13(4), 044027 (1-4) (2008)]. Here, the sample is illuminated using a white light source and the scattered/reflected photons after absorption is detected from the slit in front of the detector/camera. One direction the detector is used to capture the spectral information and the other direction is used to capture the lateral information along the line. By scanning the line along the sample, the spectral information along the second lateral direction is obtained. This provides with a huge hyperspectral data set illustrating a three dimensional spectral overview of the region of interest. By selecting a wavelength, respective images signifying different molecules/compounds can be obtained. This can further be used for performing ratio imaging of two different wavelengths. This modality enables faster imaging compared to point measurement imaging as described above.

The processor P may be implemented in various ways. The processor P may be integrated in a dedicated device including front-ends for the hyperspectral camera HSC and the probe PR. However, the processor P may be distributed to one or more separate computer (s) or processor system(s) remotely located from the camera HSC and probe PR.

Figure 2:
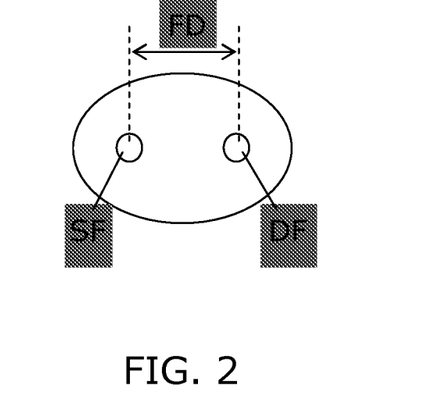
FIG. 2 illustrates a sketch of an optical probe tip suitable for the invention.

FIG. 2 illustrates a tip of a possible optical contact probe for point-based probe measurements. A source fiber end SF emits light, and a detector fiber end DF detects the reflected light. E.g. the tip could be the tip of the PR shown in FIG. 1. The two fibers end SF, DF are arranged with a centre-to-centre distance of FD. This can be used e.g. for DRS, Fluorescence or Raman spectroscopy. DRS measurements with a contact probe can be executed very fast over a continuous wavelength range, and the probed volume can extend up to several millimeters into the tissue depending on the effective source-to-detector fiber(s) distance FD (e.g. with a probing depth≈½ fiber distance). Thus, single point DRS provides an enhanced sensitivity and specificity compared to hyperspectral imaging by measuring over a wavelength range extending into the NIR (e.g. from 400 nm to 1600 nm), which can include major contributions from additional tumor discriminators. See also [R. Nachabé, D. Evers, B H W Hendriks, G W Lucassen, M. Van der Voort, E J Rutgers, M-J Vrancken Peeters, J A van der Hage, H S Olderburg, J. Wesseling and T J M Ruers, "Diagnosis of breast cancer using optical spectroscopy from 500 to 1600 nm: a comparison of classification methods, J. Biomed. Opt. 16 (2011) p 087010.].

Figure 3:
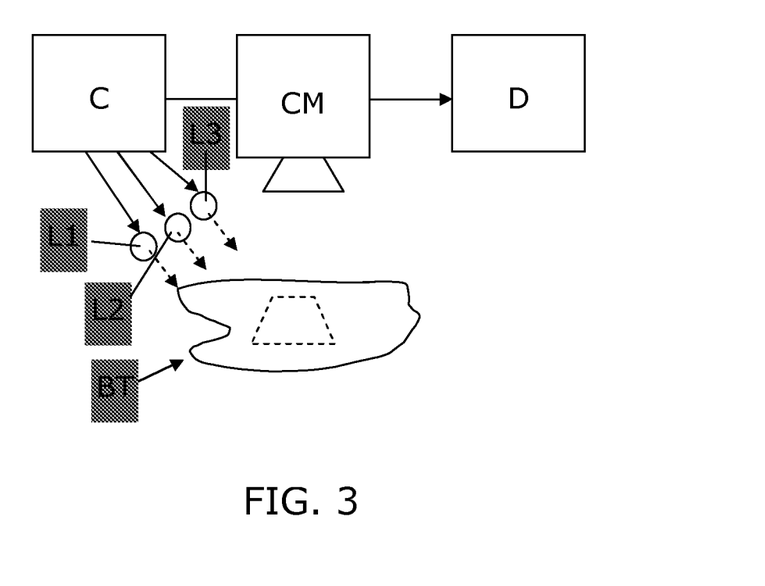
FIG. 3 illustrates a hyperspectral camera system embodiment based on a normal camera and with different narrow band wavelength light sources.

FIG. 3 illustrates a hyperspectral camera system based on a normal digital camera CM which provides 2D images of the biological tissue BT in a sequential manner controlled by a controller, where light sources L1, L2, and L3 sequentially applies their different narrow band light to the surface of the biological tissue BT. Often it is possible to achieve a good discrimination between tissue types by measuring reflectivity at only a few carefully selected wavelengths, and using some basic techniques to create contrast like dividing reflectivity at two different wavelengths. With such system it is possible to replace the expensive hyperspectral camera with a normal camera CM and use various narrow-band light sources instead. Preferably, biological tissue BT is located in a dark place during the sequential illumination by light sources L1-L3 to avoid any interference from other light sources.

Figure 4A:
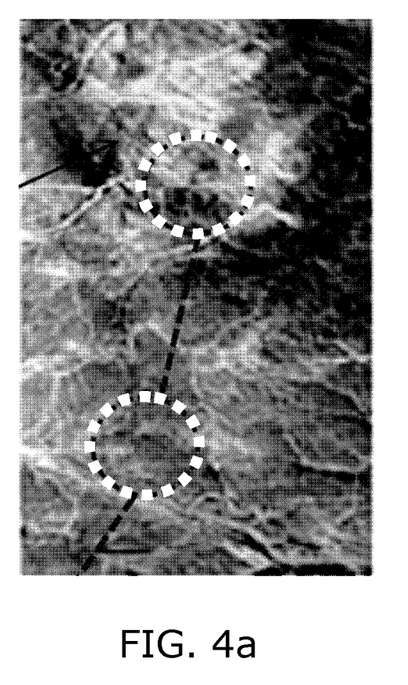
FIG. 4a illustrates a visualization of a hyperspectral image with indications of suspicious areas where tumor tissue may be present.
Figure 4B:
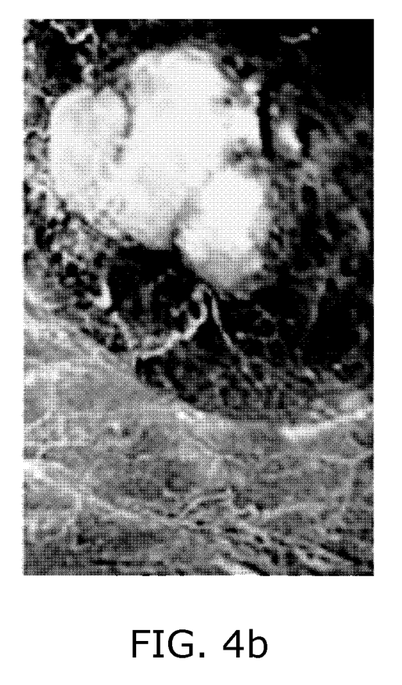
FIG. 4b illustrates the image of FIG. 4a after the hyperspectral processing algorithm has been calibrated, thus revealing clearly tumor as a white shading.

FIGS. 4a and 4b show a constructed illustration of the same hyperspectral image before (FIG. 4a) and after (FIG. 4b) calibration of the hyperspectral processing algorithm. In the hyperspectral image FIG. 4a, suspicious areas which cannot be unambiguously classified by the hyperspectral image processing can be visually indicated to an operator, here illustrated as two areas indicated by dashed white lines. This is a guide to the operator to perform probe measurements within these suspicious areas, e.g. using a point measurement probe. The increased sensitivity and specificity of such point measurements for (residual) tumor discrimination can be used to recalibrate the hyperspectral processing image, e.g. a look-up table used therein, and thereby essentially enhancing the sensitivity and specificity of each pixel in the hyperspectral image. The result of such calibration is clearly seen in FIG. 4b, where the upper area in FIG. 4a is seen to actually hide a tumor (white shading) which is clearly indicated in FIG. 4b, whereas the lower are indicated as suspicious in FIG. 4a is seen in the enhanced image of FIG. 4b not to include tumor tissue.

The point probe can also be used with fluorescence spectroscopy, which allows for enhanced tumor discrimination, e.g. by providing further information on the local metabolism, such as NAD+/NADH ratio, or the presence of autofluorescent tumor-specific markers in the tissue, such as cytostatic drugs like doxorubicin or paclitaxel. Using Raman spectroscopy, chemical constituents associated with the presence of tumor cells can be identified with a very high accuracy and can give complement information for the recalibration of the hyperspectral processing algorithm.

Figure 5A:
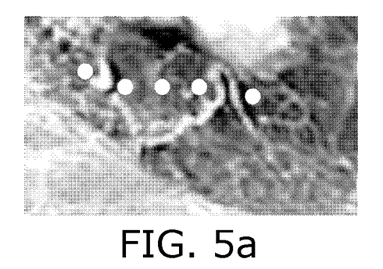
FIGS. 5a-5c illustrate different strategies for selecting location of point measurement with a probe.
Figure 5B:
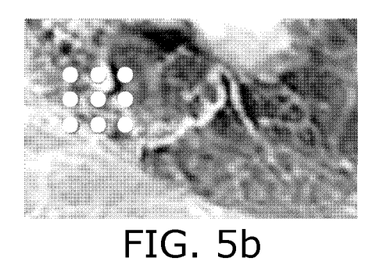
Figure 5C:
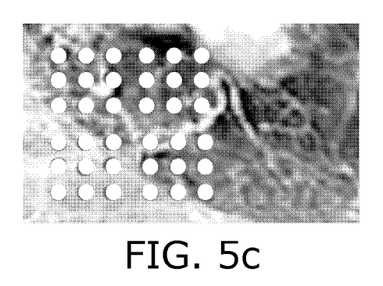

FIGS. 5a-5c show examples of different strategies for probe measurements with point or at least small area measurements serving to cover a larger area. FIG. 5a shows point measurements, while FIGS. 5b and 5c show clusters of points covering a region of interest. E.g. the strategy shown in FIGS. 5b and 5c can be obtained using a combination of a single point probe and a scanning fiber microscope. Thus, in some embodiments, the probe may comprise both a single point probe and a scanning fiber microscope [B H W Hendriks, W C J Bierhoff, J J L Horikx, A E Desjardins, C A Hezemans, G W 't Hooft, G W Lucassen, and N Mihajlovic, "High-resolution resonant and non resonant fiber-scanning confocal microscope", J. Biomed. Opt. 16 (2011) p 026007]. Such scanning fiber microscope enables confocal imaging of the biological tissue under examination with a significant spatial resolution, field of view (FOV), and contrast. The combination in addition to the hyperspectral image provides a significant advancement over a single point measurement, e.g. as FIG. 5a. This modality enables multi-spectral imaging, full wavelength regions, over a spatial region of interest (~200 μm) with a submicron resolution (~0.6 μm). The modality can be used to obtain full spectral information either from a single region of interest, such as shown in FIG. 5b, or in combination as shown in FIG. 5c to cover many individual regions of interested, thus allowing information of a significantly larger region.

The combination probe system could further employ different optical imaging modalities to be readily implemented such as confocal reflectance [K. Carlson, M. Chidley, K-B. Sung, M. Descour, A. Gillenwater, M. Follen, and R. Richards-Kortum, "In vivo fiber-optic confocal reflectance microscope with an injection-molded plastic miniature objective lens," Appl. Opt. 44(10), 1792-1797 (2005)], confocal fluorescence [J. C. Jung, A. D. Mehta, E. Aksay, R. Stepnoski, and M. J. Schnitzer, "In vivo mammalian brain imaging using one- and two-photon fluorescence microendoscopy," J. Neurophysiol. 92(5), 3121-3133 (2004)], two-photon fluorescence [J. C. Jung and M. J. Schnitzer, "Multiphoton endoscopy," Opt. Lett. 28(11), 902-904 (2003)] and [M. T. Myaing, D. J. MacDonald, and X. Li, "Fiber-optic scanning two-photon fluorescence endosocope," Opt. Lett. 31(8), 1076-1078 (2006)], and optical coherence tomography [G. J. Tearney, M. E. Brezinski, B. E. Bouma, S. A. Boppart, C. Pitris, J. F. Southern, and J. G. Fujimoto, "In vivo endoscopic optical biopsy with optical coherence tomography," Science 276(5321), 2037-2039 (1997)], could enable better characterization of the sample under examination.

Figure 6:
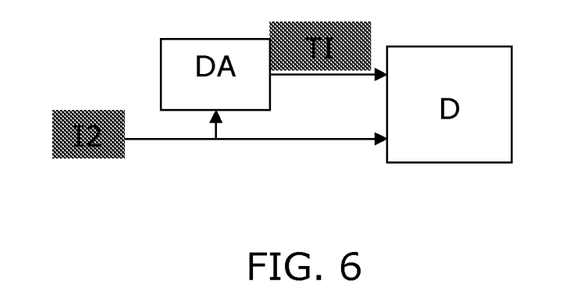
FIG. 6 illustrates a block diagram of a diagnostic embodiment where a tumor indication is shown on a display together with the hyperspectral image after calibration.

FIG. 6. illustrates a diagnostic embodiment where, referring to FIG. 1, the hyperspectral image 12 after calibration of the hyperspectral image algorithm HSA is applied to the display D. A diagnosis algorithm DA processes the same image 12 and detects therein the area where the target structure is probable to be, e.g. a tumor. A target indicator TI is then applied to the display, e.g. a highlighting in the form of a color, a shading, a line around the area or the like.

In the following, examples details regarding the extraction of features of parameters from the one or more probe measurement data will be described. An example of extracting the physiological parameter is by fitting the acquired spectra using a custom made Matlab 7.9.0 (Mathworks, Natick, Mass.) algorithm. In this algorithm, a widely accepted analytical model was implemented, namely the model introduced by the reference [T. J. Farrel, M. S. Patterson and B. C. Wilson, "A diffusion theory model of spatially resolved, steady-state diffuse reflectance for the non-invasive determination of tissue optical properties," Med. Phys. 19 (1992) p. 879-888], which is hereby incorporated by reference in entirety. The input arguments for the model of the reference [T. J. Farrel, M. S. Patterson and B. C. Wilson, "A diffusion theory model of spatially resolved, steady-state diffuse reflectance for the non-invasive determination of tissue optical properties," Med. Phys. 19 (1992) p. 879-888] are the absorption coefficient $\mu_a(\lambda)$, the reduced scattering coefficient $\mu'_s(\lambda)$ and the center-to-center distance between the emitting and collecting fibers at the tip of the probe. For the camera image there is no fiber distance and the model of Farrel is no longer applicable. Instead it is possible to use algorithms based on the well-known Kubelka-Munk model. An example of how reflectivity is derived from scattering and absorption properties is given e.g. in [M. Müller, G. F. Zhou "Modeling electrophoretic paper-like displays", Proc. IDW 1-3, 1287-1290 (2007)]) For a complete description of the diffusion theory model, we refer to [T. J. Farrel, M. S. Patterson and B. C. Wilson, "A diffusion theory model of spatially resolved, steady-state diffuse reflectance for the non-invasive determination of tissue optical properties," Med. Phys. 19 (1992) p. 879-888].

In the following part, the model will be explained briefly. The used formulas are mainly based on work of Nachabé et al., and reference is thus made to [R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm," Optics Express, vol. 18, 2010, pp. 879-888] which is hereby incorporated by reference in entirety, and furthermore reference is made to [R. Nachabé, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm," Journal of Biomedical Optics, vol. 15, May. 2010, pp. 037015-10] which is hereby incorporated by reference in entirety.

A double power law function can be used to describe the wavelength dependence of the reduced scattering, where the wavelength $\lambda$ is expressed in nm and is normalized to a wavelength value of $\lambda_0=800$ nm. The parameter a corresponds to the reduced scattering amplitude at this specific wavelength.

$$\mu_s(\lambda) = a\left(\rho_{MR}\left(\frac{\lambda}{\lambda_0}\right)^{-b} + (1-\rho_{MR})\left(\frac{\lambda}{\lambda_0}\right)^{-4}\right)[cm^{-1}] \quad (Eq. 1)$$

In this equation the reduced scattering coefficient is expressed as the sum of Mie and Rayleigh scattering where $\rho_{MR}$ is the Mie-to-total reduced scattering fraction. The reduced scattering slope of the Mie scattering is denoted b and is related to the particle size.

Figure 7:
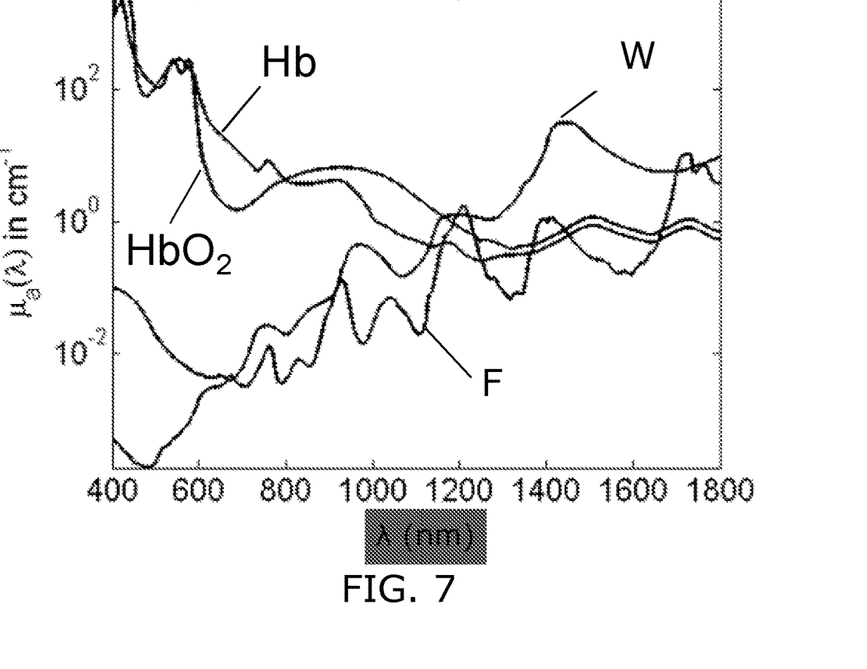
FIG. 7 illustrates a graph showing absorption spectra for blood, water and fat.

FIG. 7 shows logarithmic plots of absorption spectra for blot Hb, $HbO_2$, water W, and fat F. For a homogeneous distribution of absorbers, the total light absorption coefficient $\mu_a(\lambda)$ can be computed as products of the extinction coefficients and volume fraction of the absorbers shown in FIG. 7:

$$\mu_a^{Total} = f_1\mu_a^1 + f_2\mu_a^2 + f_3\mu_a^3 + \quad (Eq. 2)$$

Instead of modeling the absorption coefficient $\mu_a(\lambda)$ as the sum of absorption coefficients weighted by the respective concentrations of the four chromophores of interest, it was decided to express the tissue absorption coefficient as:

$$\mu_a^{Tissue}(\lambda) = C(\lambda)\nu_{Blood}\mu_a^{Blood}(\lambda)(+\nu_{WL}\mu_a^{WL}(\lambda) \; [cm^{-1}] \quad (Eq. 3)$$

where $\mu_a^{Blood}(\lambda)$ corresponds to the absorption by blood and $\mu_a^{WL}(\lambda)$ corresponds to absorption by water and lipid together in the probed volume. The volume fraction of water and lipid is $\nu_{WL}=[Lipid]+[H_2O]$, whereas $\nu_{Blood}$ represents the blood volume fraction for a concentration of hemoglobin in whole blood of 150 mg/ml.

The factor C is a wavelength dependent correction factor that accounts for the effect of pigment packaging and alters for the shape of the absorption spectrum. This effect can be explained by the fact that blood in tissue is confined to a very small fraction of the overall volume, namely blood vessels. Red blood cells near the center of the vessel therefore absorb less light than those at the periphery. Effectively, when distributed homogeneously within the tissue, fewer red blood cells would produce the same absorption as the actual number of red blood cells distributed in discrete vessels. The correction factor can be described as:

$$C(\lambda) = \frac{1-\exp(-2R\mu_a^{Blood}(\lambda))}{2R\mu_a^{Blood}(\lambda)}, \quad (Eq. 4)$$

where R denotes the average vessel radius expressed in cm. The absorption coefficient related to blood is given by:

$$\mu_a^{Blood}(\lambda) = \alpha_{BL}\mu_a^{HbO_2}(\lambda) + (1-\alpha_{BL})\mu_a^{Hb}(\lambda) \; [cm^{-1}] \quad (Eq. 5)$$

where $\mu_a^{HbO_2}(\lambda)$ and $\mu_a^{Hb}(\lambda)$ represent the basic extinction coefficient spectra of oxygenated hemoglobin $HbO_2$ and deoxygenated hemoglobin Hb, respectively. The oxygenated hemoglobin fraction in the total amount of hemoglobin is noted $\alpha_{SL}=[HbO_2]/([HbO_2]+[Hb])$ and is commonly known as the blood oxygen saturation.

The absorption due to the presence of water and lipid in the measured tissue is defined as:

$$\mu_a^{WL}(\lambda) = \alpha_{WL}\mu_a^{Lipid}(\lambda) + (1-\alpha_{WL})\mu_a^{H_2O}(\lambda) \; [cm^{-1}] \quad (Eq. 6)$$

In this case the concentration of lipid related to the total concentration of lipid and water together can be written as $\alpha_{WF}=[Lipid]/([Lipid]+[H_2O])$, where [Lipid] and [$H_2O$], correspond to the concentration of lipid (density of 0.86 g/ml) and water, respectively.

This way of relating the water and lipid parameters in the expression of the absorption coefficient defined in Eq. 6, rather than estimating separately the water and lipid volume fraction corresponds to a minimization of the covariance of the basic functions for fitting resulting in a more stable fit cf the reference [R. Nachabé, B. H. W. Hendriks, M. V. D. Voort, A. E, and H. J. C. M. Sterenborg, "Estimation of biological chromophores using diffuse optical spectroscopy: benefit of extending the UV-VIS wavelength range to include 1000 to 1600 nm," Optics Express, vol. 18, 2010, pp.

879-888]. For further explanation and validation of this theorem reference is made to [R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm," Journal of Biomedical Optics, vol. 15, May. 2010, pp. 037015-10], which is hereby included by reference in entirety.

Another way to discriminate differences in spectra is by making use of a principal components analysis. This method allows classification of differences in spectra and thus allows discrimination between tissues. It is also possible to extract features from the spectra.

Figure 8:
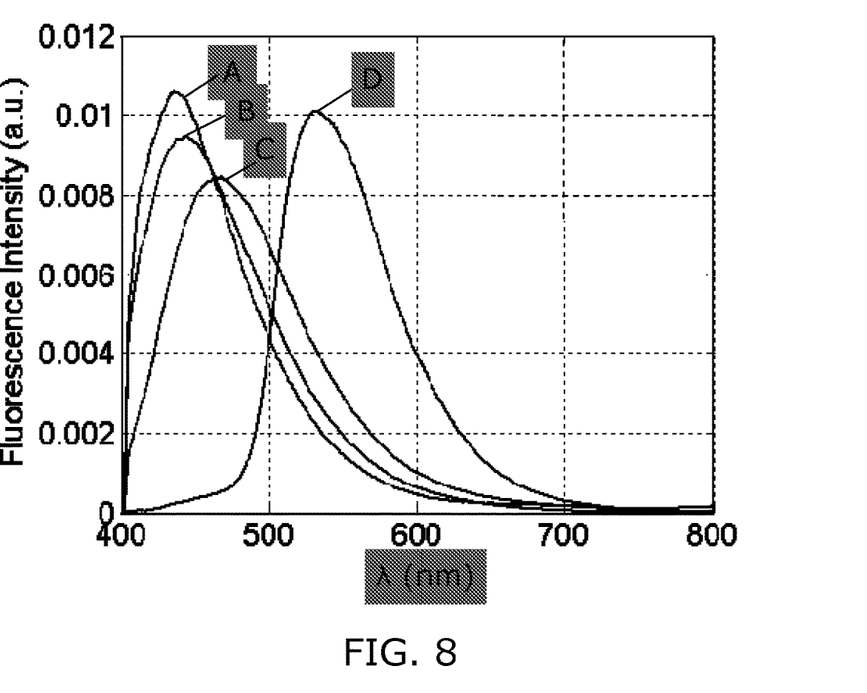
FIG. 8 illustrates a graph showing intrinsic fluorescence curves for A: collagen, B: elastin, C: NADH, and D: FAD.

FIG. 8 shows intrinsic fluorescence curves for A: Collagen, B: Elastin, C: NADH, and D: FAD. Such parameters could also be measured with a probe. Especially, the ratio NADH/FAD, which is called the optical redox parameter, could be calculated, since this ratio is an indicator for the metabolic state of the tissue, which is assumed to change upon effective treatment of cancer cells, see e.g. [Q. Zhang, M. G. Mueller, J. Wu and M. S. Feld, "Turbidity-free fluorescence spectroscopy of biological tissue" Opt. Lett. 25 (2000) p 1451].

Figure 9:
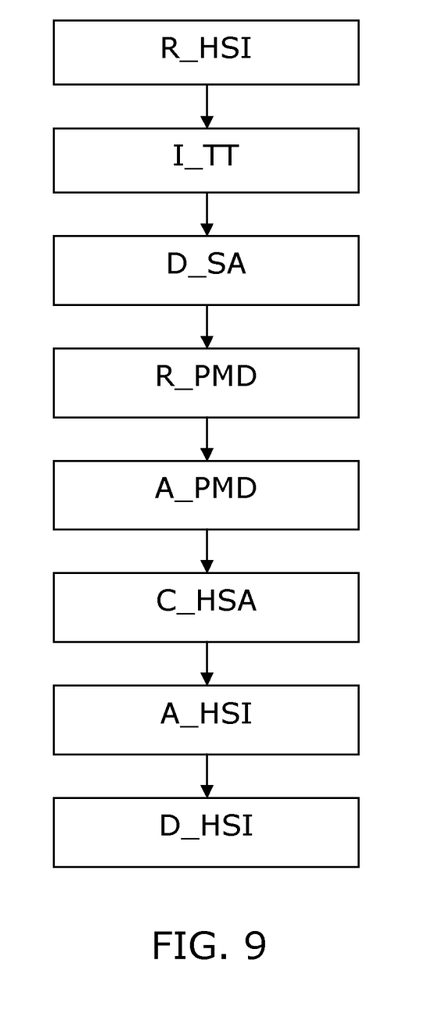
FIG. 9 illustrates a block diagram of a method embodiment.

FIG. 9 illustrates a method embodiment according to the invention for identifying possible tumor tissue within a human or animal tissue. The method comprises the step R HSI of receiving a hyperspectral image of a first area of the tissue under test, optionally also the step of providing the hyperspectral image with a hyperspectral camera. The hyperspectral image is then analyzed L_TT with an algorithm for identifying and/or localizing a part or parts of the hyperspectral image which may contain tumor tissue. In case such suspicious areas are localized in the hyperspectral image, the next step D_SA is displaying the hyperspectral image with indication of the suspicious areas, e.g. using a line or other graphical symbol overlaid the hyperspectral image. In this step D_SA, the hyperspectral image is processed with an initial setting or calibration of a hyperspectral image algorithm, e.g. a setting selected based on the target structure, in this case tumor tissue, to be identified. The operator then has a visual indication of which parts of the tissue under test to perform probe measurements. The next step R_PMD is receiving probe measurement data, optionally also the step of providing the probe measurements resulting in the probe measurement data. E.g. the probe measurement data are obtained with an optical surface probe providing measurement data in a second area being essentially in one point within the first area, preferably within the suspicious area identified and displayed.

The probe measurement data is then analyzed A_PMD with an algorithm arranged to identify one or more physiological parameters, e.g. based on a measured optical absorption coefficient, the reduced scattering coefficient and the center-to-center distance between light emitting and collecting fibers at the tip of the probe. The result is then used for calibrating C_HSA the processing algorithm used to analyze the hyperspectral image, so as to adapt the processing algorithm to provide an image with an enhanced contrast between target structure, in this example tumor tissue, and the tissue under test. Subsequently, the hyperspectral image is analyzed A HSI using the calibrated hyperspectral image processing algorithm. Finally, the re-analyzed hyperspectral image is displayed D HSI, e.g. on a color monitor.

In this way one or a few point measurements with a high spectral resolution can be utilized to add information about the tissue in suspicious areas of the standard-processed hyperspectral image so as to modify the hyperspectral processing algorithm. This is then used to process the hyperspectral image in order to provide an image with enhanced contrast or sensitivity towards distinguishing between the tissue under test and the target structure, e.g. tumor tissue. Hereby, the method assists the operator, e.g. a medical doctor or other medical staff, in evaluating whether tumor tissue is present within an area under test, e.g. in the search for positive margins. Additionally, the method may include indicating suspicious areas also in the re-analyzed hyperspectral image, and/or indicating the probability of tumor tissue being present.

It is to be understood that some of the steps may be performed in a different order than shown in FIG. 9 and than in the description of the above method embodiment.

To sum up, the invention provides a medical imaging system for identifying a target structure, e.g. a tumor, in a biological tissue. A hyperspectral camera system is used for imaging a surface area of the tissue, e.g. with a limited spectral resolution, but enough to allow identification of suspicious areas where the target structure may be, e.g. such areas can be visually indicated on a display to the operator. A probe, e.g. an optical surface probe, is used to provide probe measurement of a smaller surface area of the tissue, but with more information indicative of the target structure. The probe is selected to provide a higher specificity with respect to identification of the target structure than the hyperspectral camera. The hyperspectral processing algorithm is then calibrated based on probe measurement data performed within the suspicious areas, thus providing a calibrated hyperspectral processing algorithm resulting in images with an enhanced sensitivity to identify the target structure. Only few probe measurements are required to significantly improve the resulting image, thereby providing a reliable and fast target structure identification.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical imaging system arranged to identify a target structure in a biological tissue, the medical imaging system comprising:
    a hyperspectral camera system arranged to provide a hyperspectral image and configured to cover a first surface area of the biological tissue, wherein pixels of the hyperspectral image include information at different light wavelength bands,
    a probe arranged to provide a probe measurement of a second surface area of the biological tissue within the first surface area of the biological tissue, and to generate probe measurement data accordingly, the probe being arranged so the second surface area covered is smaller than the first surface area that is covered by the hyperspectral camera system, wherein the probe is selected to provide a higher specificity with respect to identification of the target structure than the hyperspectral camera system, and a processor connected to receive the hyperspectral image and the probe measurement data, wherein the processor is arranged to:
analyze the hyperspectral image according to a hyperspectral processing algorithm to identify a part of the hyperspectral image which includes a suspect area indicative of the target structure,
receive the probe measurement data, wherein the measured second surface area is within the suspect area,
process the hyperspectral image according to an image processing algorithm to identify a tip of the probe in the hyperspectral image, to identify as to which part of the hyperspectral image the probe measurement data corresponds,
analyze the probe measurement data according to a probe processing algorithm comprising calculating a plurality of measurement parameters and translating the plurality of measurement parameters into physiological parameters, wherein the physiological parameters confirm that the measured second surface area include the target structure,
calibrate the hyperspectral processing algorithm based on the physiological parameters by refining a grouping of pixels in the hyperspectral image which are identified in the probe measurement data, and confirmed by the physiological parameters, as belonging to the target structure, and
provide a calibrated hyperspectral processing algorithm with an enhanced sensitivity to identify the target structure in the hyperspectral image, and a display arranged to visually display the probe in the hyperspectral image and visually display the hyperspectral image after being processed with the calibrated hyperspectral processing algorithm.

2. The medical imaging system according to claim 1, wherein the probe is further arranged to provide a probe measurement with a higher spectral resolution than the hyperspectral image.

3. The medical imaging system according to claim 1, wherein the display is arranged to visually display the hyperspectral image after being processed with the hyperspectral processing algorithm together with a visual indication of the part which is identified as containing suspect area indicative of the target structure.

4. The medical imaging system according to claim 1, wherein the processor is arranged to analyze the probe measurement data according to a probe processing algorithm comprising comparing the probe measurement data with a look-up-table.

5. The medical imaging system according to claim 1, wherein the probe comprises one of: a surface probe, and an interventional device.

6. The medical imaging system according to claim 1, wherein the probe comprises at least one of: an optical probe, and an ultrasound probe.

7. The medical imaging system according to claim 1, wherein the probe comprises one of: a diffuse reflectance spectroscopy probe, a diffuse optical tomography probe, a differential path length spectroscopy, a fluorescence probe, a Raman spectroscopy probe, a confocal reflectance probe, a confocal fluorescence probe, a two-photon fluorescence probe, an optical coherence tomography probe, and a scanning fiber microscope arranged to perform confocal imaging.

8. The medical imaging system according to claim 1, wherein the hyperspectral camera system comprises one of:
a hyperspectral camera arranged to provide the hyperspectral image,
a camera and a plurality of light sources with different narrow band wavelengths arranged to provide images with the associated biological tissue sequentially illuminated by the plurality of light sources, and
a camera and a tunable optical filter arranged between the camera and the associated biological tissue, so as to provide sequential images with different settings of the tunable optical filter.

9. The medical imaging system according to claim 1, wherein the target structure is one of: tumor tissue, a nerve bundle, a blood vessel, lymph nodes, and oxygenation level of tissue.

10. A method for detecting a target structure in a biological tissue, the method comprising:
providing, by a hyperspectral camera system, a hyperspectral image covering a first surface area of the biological tissue, wherein pixels of the hyperspectral image include information regarding different light wavelength bands,
providing, by a probe, probe measurement data in accordance with a probe measurement of a second surface area of the biological tissue within the first surface area of the biological tissue, wherein the probe measurement is selected to provide a higher specificity with respect to identification of the target structure than the hyperspectral camera system,
arranging the probe so the second surface area covered is smaller than the first surface area that is covered by the hyperspectral camera system,
generating probe measurement data after the arranging,
analyzing, by a processor, the hyperspectral image according to a hyperspectral processing algorithm to identify a part of the hyperspectral image which includes a suspect area indicative of the target structure,
receiving, by the processor, the probe measurement data, wherein the measured second surface area is within the suspect area,
processing, by the processor, the hyperspectral image according to an image processing algorithm to identify a tip of the probe in the hyperspectral image, to identify as to which part of the hyperspectral image the probe measurement data corresponds,
analyzing, by the processor, the probe measurement data according to a probe processing algorithm comprising calculating a plurality of measurement parameters and translating the plurality of measurement parameters into physiological parameters, wherein the physiological parameters confirm that the measured second surface area includes the target structure,
calibrating, by the processor, the hyperspectral processing algorithm based on the physiological parameters by refining a grouping of pixels in the hyperspectral image which are identified in the probe measurement data, and confirmed by the physiological parameters, as belonging to the target structure, providing, by the processor, a calibrated hyperspectral processing algorithm with an enhanced sensitivity to identify a target tissue structure in the hyperspectral image, and displaying, by a display, the hyperspectral image after being processed with the calibrated hyperspectral processing algorithm.

11. The method according to claim 10, further comprising providing a probe measurement with a higher spectral resolution than the hyperspectral image.

12. The method according to claim 10, further comprising, by the processor, analyzing the probe measurement data according to a probe processing algorithm comprising comparing the probe measurement data with a look-up-table data.

13. The method according to claim 10, wherein the probe comprises one of: a diffuse reflectance spectroscopy probe, a diffuse optical tomography probe, a differential path length spectroscopy, a fluorescence probe, a Raman spectroscopy probe, a confocal reflectance probe, a confocal fluorescence probe, a two-photon fluorescence probe, an optical coherence tomography probe, and a scanning fiber microscope arranged to perform confocal imaging.

14. A medical imaging system arranged to identify a target structure in a biological tissue, the medical imaging system comprising:
  a hyperspectral camera system arranged to provide a hyperspectral image configured to cover a first surface area of the biological tissue, wherein pixels of the hyperspectral image include information at different light wavelength bands;
  a probe arranged to provide a probe measurement of a second surface area of the biological tissue within the first surface area of the biological tissue, and to generate probe measurement data accordingly, the probe being arranged so the second surface area covered is smaller than the first surface area that is covered by the hyperspectral camera system, wherein the probe is selected to provide a higher specificity with respect to identification of the target structure than the hyperspectral camera system; and
  a tangible and non-transitory memory that stores instructions, which when executed by a processor cause the processor to:
    analyze the hyperspectral image according to a hyperspectral processing algorithm to identify a part of the hyperspectral image which includes a suspect area indicative of the target structure;
    receive the probe measurement data, wherein the measured second surface area is within the suspect area;
    process the hyperspectral image according to an image processing algorithm to identify a tip of the probe in the hyperspectral image, to identify as to which part of the hyperspectral image the probe measurement data corresponds;
    analyze the probe measurement data according to a probe processing algorithm comprising calculating a plurality of measurement parameters and translating the plurality of measurement parameters into physiological parameters, wherein the physiological parameters confirm that the measured second surface area include the target structure, calibrate the hyperspectral processing algorithm based on the physiological parameters by refining a grouping of pixels in the hyperspectral image which are identified in the probe measurement data, and confirmed by the physiological parameters, as belonging to the target structure, and provide a calibrated hyperspectral processing algorithm with an enhanced sensitivity to identify the target structure in the hyperspectral image; and
  a display arranged to visually display the probe in the hyperspectral image and visually display the hyperspectral image after being processed with the calibrated hyperspectral processing algorithm.

15. The medical imaging system according to claim 14, wherein the
  tangible and non-transitory memory that stores further instructions, which when executed by the processor cause the processor to:
    analyze the probe measurement data according to a probe processing algorithm comprising comparing the probe measurement data with a look-up-table.

16. The medical imaging system according to claim 14, wherein the probe is further arranged to provide a probe measurement with a higher spectral resolution than the hyperspectral image.

17. The medical imaging system according to claim 14, wherein the display is arranged to visually display the hyperspectral image after being processed with the hyperspectral processing algorithm together with a visual indication of the part which is identified as containing suspect area indicative of the target structure.

18. The medical imaging system according to claim 14, wherein the probe comprises one of: a surface probe, and an interventional device.

19. The medical imaging system according to claim 14, wherein the probe comprises at least one of: an optical probe, and an ultrasound probe.

20. The medical imaging system according to claim 14, wherein the probe comprises one of: a diffuse reflectance spectroscopy probe, a diffuse optical tomography probe, a differential path length spectroscopy, a fluorescence probe, a Raman spectroscopy probe, a confocal reflectance probe, a confocal fluorescence probe, a two-photon fluorescence probe, an optical coherence tomography probe, and a scanning fiber microscope arranged to perform confocal imaging.

\* \* \* \* \*